United States Patent [19]

Saran

[11] Patent Number: 5,001,250

[45] Date of Patent: Mar. 19, 1991

[54] PURIFICATION OF BIDENTATE ORGANOPHOSPHOROUS EXTRACTANTS

[75] Inventor: Mohan S. Saran, Grand Island, N.Y.

[73] Assignee: Occidental Chemical Corporation, Niagara Falls, N.Y.

[21] Appl. No.: 358,226

[22] Filed: May 30, 1989

[51] Int. Cl.$^5$ .............................................. C07F 9/02
[52] U.S. Cl. .................................. 558/146; 558/170; 564/15
[58] Field of Search ...................... 558/146, 171, 170; 564/15

[56] References Cited

U.S. PATENT DOCUMENTS

| | | | |
|---|---|---|---|
| 4,038,329 | 7/1977 | Palmer | 558/146 |
| 4,165,360 | 8/1979 | Casper et al. | 558/170 |
| 4,760,166 | 7/1988 | Stautzenberger | 558/170 |

FOREIGN PATENT DOCUMENTS 35595 2/1982 Japan .................................. 558/146

1171385 1/1967 United Kingdom ................ 558/146

*Primary Examiner*—Mukund J. Shah
*Assistant Examiner*—E. L. Ward
*Attorney, Agent, or Firm*—James F. Tao; Richard D. Fuerle

[57] ABSTRACT

Crude N,N-dialkylcarbamoylmethylphosphonates and phosphine oxide extractants, and particularly crude dihexyl N,N-diethylcarbamoylmethylphosphonate and octylphenyl N,N-diisobutylcarbamoyl phosphine oxide, are purified by distilling the crude materials in a thin film evaporator. Preferably, the crude dihexyl N,N-diethylcarbamoylmethylphosphonate is reacted with concentrated hydrochloric acid and subsequently reacted with aqueous sodium hydroxide prior to distillation in the thin film evaporator to hydrolyze impurities contained in the crude product. The purified extractants are useful for extracting actinides and lanthanides from liquid waste streams.

17 Claims, No Drawings

PURIFICATION OF BIDENTATE ORGANOPHOSPHOROUS EXTRACTANTS

BACKGROUND OF THE INVENTION

This invention relates to the use of a thin film evaporator to purify N,N-dialkylcarbamoylmethyl phosphonates and phosphine oxides. In particular, it relates to the use of a thin film evaporator to purify dihexyl N,N-diethylcarbamoylmethylphosphonate (CMP) and octylphenyl N,N-diisobutylcarbamoyphosphine oxide (CMPO).

The use of monodentate and bidentate organophosphorus ligands as extractants for actinides and lanthanides is well-known in the extractant art. Typical monodentate ligands include tributyl phosphate and dibutylbutyl phosphonate. These monodentate ligands are effective for extracting uranium, neptunium, and plutonium from typical nitric acid solutions. However, the monodentate ligands are incapable of extracting americium and curium from nitric acid solutions due to extensive co-extraction of nitric acid into the organic phase, resulting in back-salting.

Unlike the monodentate ligands, bidentate organophosphorus ligands are superior for extracting actinides and lanthanides, and are thus useful for removing lanthanides and actinides from liquid wastes generated by processing or reprocessing nuclear fuels and from weapons production. In particular, CMP has been used in processes designed to separate the biologically hazardous radioactive actinide elements with long half-lives from the bulk of process wastes. For instance, a 30% solution of CMP in various solvents is effective for removing greater than 99% of the americium and plutonium from the waste streams at a plutonium reclamation facility. However, the lack of availability of bidentate extractants such as CMP in high purity has hampered the commercialization of such processes.

It is known that dialkyl N,N-dialkylcarbamoylmethyl-phosphonates can be prepared in 40% to 60% yield by the Arbuzov reaction of trialkyl phosphites with N,N-diethyl bromoacetamides. But the quality of the product produced from this reaction is generally poor due to the decomposition of the product and to accompanying side reactions.

In the Michaelis reaction a dialkylphosphite can also be used:

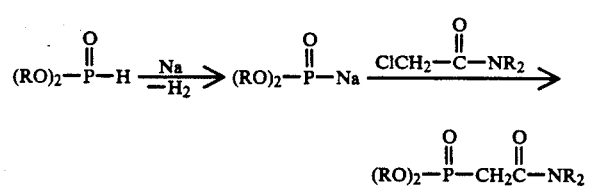

That reaction also suffers from a low yield due to the slow dissolution of sodium.

U.S. Pat. No. 4,396,556, issued Aug. 2, 1983, to Kem, uses a variation of the Michaelis reaction employing aqueous sodium hydroxide as the base and a phase-transfer catalyst such as methyl tricaprylylammonium chloride to avoid hydrolysis of the reactants and products. The process of this reference provides for the preparation of carbamoylmethylphosphonates using phase transfer catalysis under reaction conditions that avoid the degradative hydrolysis of products and reactants.

Although various processes are effective in producing bidentate organophosphorus extractants in good yield, the final products frequently include amounts of impurities which exceed the specifications required for their use in critical applications such as the removal of radioactive actinides from liquid wastes. The present invention is directed to the purification of such extractants to meet these standards.

SUMMARY OF THE INVENTION

I have discovered that N,N-dialkylcarbamoylmethylphosphonates and phosphine oxide extractants purified by thin film evaporation have coefficients of back extraction for americium about 8 to 25 times better than the same extractants purified by conventional small scale distillation.

DETAILED DESCRIPTION OF THE INVENTION

The purification process of this invention is applicable to N,N-dialkylcarbamoylmethylphosphonates and phosphine oxides extractants of the general formula:

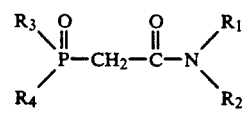

where $R_1$ and $R_2$ are each independently selected from alkyl from $C_1$ to $C_8$, and preferably from $C_2$ to $C_4$, $R_3$ and $R_4$ are R or RO, where each R is independently selected from alkyl, aryl, aralkyl, and alkaryl from $C_1$ to $C_{15}$, and preferably from $C_4$ to $C_8$. If $R_1$, $R_2$, $R_3$, and $R_4$ contain more carbon atoms than specified the extractant becomes less soluble in solvents, and fewer carbon atoms than specified make the compound more water soluble and less useful as an extractant.

The extractants can be prepared by a variety of methods, but are preferably prepared by reacting a phosphonate or phosphine oxide with an N,N-dialkyl haloacetamide:

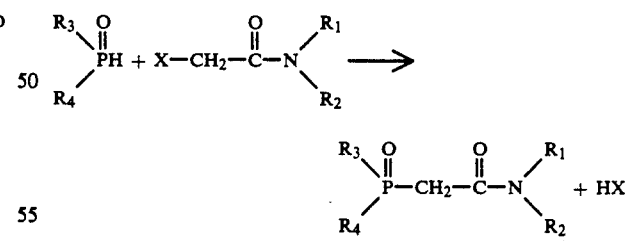

where X is halogen, preferably chlorine.

The purification process of this invention will now be illustrated with two particularly preferred extractants, CMP and CMPO.

Preparation of Dihexyl N,N-diethylcarbamoylmethylphosphonate

Crude dihexyl N,N-diethylcarbamoylmethylphosphonate (CMP) can be prepared by the reaction of dihexylphosphite, N,N-diethylchloroacetamide and aqueous sodium hydroxide in a two-phase system

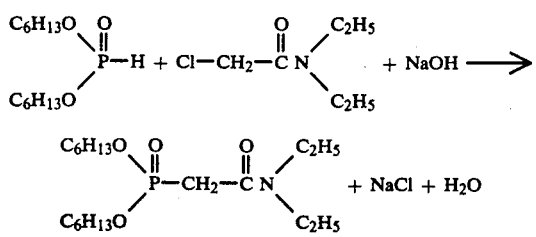

A phase transfer catalyst is used in this reaction. A phase transfer catalyst is a catalyst that is soluble in one phase but reacts at the interface of the phases to form a new compound also soluble in that phase. Examples of phase transfer catalysts useful in this invention include quaternary ammonium compounds and quarternary phosphonium compounds, preferably compounds of the formula $(Z)_4NX'$ or $(Z)_4PX'$ where Z can be the same or different and is selected from alkyl groups containing 1–18 carbon atoms. (See U.S. Pat. No. 4,396,556, the disclosure of which is herein incorporated by reference.) A particularly useful catalyst is methyl tricaprylylammonium chloride, which is commercially available from the Ashland Chemical Company under the designation "Adogen 464."

The CMP produced as described above contains several major impurities such as hexanol, N,N-diethylchloroacetamide, and various organic impurities which are present in varying degrees. Unfortunately, however, CMP is thermally unstable and undergoes decomposition during distillation. In small scale distillations, such as in the laboratory, the decomposition, while significant, is not substantial. However, as large quantities are distilled which require more prolonged distillation, such as on a commercial or semi-commercial scale, the problems of decomposition become more pronounced.

Preparation of Octylphenyl N,N-diisobutylcarbamoyl Phosphine Oxide

Crude octylphenyl N,N-diisobutylcarbamoyl phosphine oxide (CMPO) can be prepared by the reaction of octylphenyl phosphine oxide and N,N-diisobutylchloroacetamide under basic reaction conditions in the presence of a phase transfer catalyst, such as methyl tricaprylylammonium chloride, in a solvent such as methylene chloride. This crude product, like the crude CMP, contains impurities which are difficult to separate or remove using conventional technology.

Purification

In order to overcome the shortcomings of conventional distillation techniques, a thin film evaporator is employed to distill the impure products. A thin film evaporator is an evaporator that distills a liquid by spreading or pouring a thin film of the liquid on a surface heated to a temperature above the boiling point of a component in the liquid. That temperature, the evaporation (wall) temperature, is preferably about 180 to about 300° C. for the extractants of this invention. Liquid is usually re-applied to the surface at the same rate that it evaporates. The use of a thin film evaporator minimizes the time that the liquid is at high temperature and therefore minimizes the amount of heat degradation which occurs during distillation. The thin film evaporator also includes a condensor which condenses and traps the products. For the extractants of this invention the condensation temperature is preferably about 130 to about 155° C. at a preferred vacuum of less than 1.0 mm Hg. Examples of thin film evaporators include wipe film evaporators and falling film evaporators. In a wipe film evaporator the liquid is wiped with a blade, usually a rotating blade, on the hot surface. In a falling film evaporator the liquid is poured over the hot surface. A wipe film evaporator is preferred because it produces a more uniform film.

Prior to distillation using the thin film evaporator, it has also been found effective, in the case of phosphonates such as CMP, to treat the crude phosphonate first with concentrated hydrochloric acid followed by treatment with 10% aqueous sodium hydroxide. This serves to remove impurities formed as a result of side reactions occurring during the preparation of the phosphonate.

The following examples are intended to further illustrate the various aspects of the invention without being limited thereby. Various modifications can be made in the invention without departing from the spirit and scope thereof, as will be readily appreciated by those skilled in the art. Such modifications and variations are within the purview and scope of the appended claims.

EXAMPLE 1

Preparation of Dihexyl N,N-diethylcarbamoylmethylphosphonate

Into a 2-liter, 3-necked, round bottom flask equipped with a mechanical stirrer, thermometer, 250 ml pressure-equalizing dropping funnel, and inert gas fittings was placed a solution of 149.5 g (1.0M) N,N-diethylchloroacetamide and 1.5 g "Adogen 464" in 400 ml $CH_2Cl_2$ and 200 ml 50% aqueous sodium hydroxide. The solution was stirred at 200 rpm and cooled to 5°–1020 C. in an ice bath. Dihexylphosphite 250 g (1.09M) diluted with 100 ml $CH_2Cl_2$ was added dropwise from the dropping funnel. This addition took about 1 hour. An analytical sample was taken by syringe every hour, and the progress of the reaction was monitored by GC analysis to determine the disappearance of the starting materials and formation of the product. The reaction was allowed to stir another two hours after the addition of dihexylphosphite. The reaction mixture was transferred to a separatory funnel, and 200 ml of distilled water was added to facilitate the separation of the phases. The top organic layer was removed and dried over anhydrous $Na_2CO_3$. The filtered organic layer was stripped of the solvent using water suction and a bath temperature of 75° –80° C. to give a light yellow oil weighing 338.9 gms (93% yield). The product was purified by distillation under vacuum, and the fraction boiling at 155° –156° C./0.1MM Hg was collected. The GC purity of this cut was 94.2%.

EXAMPLE 2

Purification of Dihexyl N,N-diethylcarbamoylmethylphosphonate

Pilot plant produced and stripped crude CMP was purified by distillation using a Pope 6-inch wipe film evaporator unit in the laboratory. A few modifications were made to the unit. Crude CMP from Example 1 was fed to the unit using an FMI Lab Pump Model RPD. Special 5-liter flasks with drain-off valves at the bottom were used to collect the product, residue, and the volatiles. These changes enabled a continuous operation of the unit without any interruptions to add the feed or take-off product or waste. Another modification which minimized the product carry-over loss with volatiles was the placement of a stainless steel gauge in the vapor carrying outlet from the main unit. The internal condenser was heated with a hot circulating bath containing "Therminol," a heat transfer fluid sold by Monsanto.

Before starting the unit, all stop-cocks were cleaned thoroughly and greased with high vacuum grease, the volatiles trap was cooled with dry ice, and the unit was put under vacuum and tested for any leaks. Pressure reading of 0.2 mm Hg was obtained. Heat was turned on to bring the wall temperature to 225 ±5° C. The circulating hot bath was turned on to bring the condenser temperature to 136 ±2° C. The unit was allowed to stabilize at these settings for about ½ hour. This whole operation took about 1-½ hours. The wiper was turned on to a setting of 4, and the feed pump was started at a setting of 0.5 which was gradually increased to 3 over a ½ hour period. The product flask was full in about 5 hours. The product receiving stop-cock was temporarily closed, and the vacuum released with $N_2$. The stop-cock at the bottom of the product receiving flask was opened to drain 4738 gms of product into a 5-gallon product drum. The flask was evacuated to 0.2 mm Hg using a secondary vacuum pump before opening the product receiving stop-cock. The same procedure was followed for the volatile trap flask, and the residue flasks when they filled up. The unit was operated for about 9 hours, and a total of 15,801 gms of product, 3113 gms of residues, and 3334 gms of volatiles were collected. To shut off the unit, the still body heat was shut off first while reducing the crude feed rate. When the wall temperature reached below 180° C, the feed was discontinued, and the wipers and condenser heat were shut off. The vacuum was released when the temperatures cooled down to below 100° C.

Although it was possible to run the unit under different conditions, the following settings were found to give a product of desired purity without too much product loss into the residue and with a good throughput. The feed rate was adjusted to keep the other settings constant.

| | |
|---|---|
| Vacuum | = 0.1–0.4 mm Hg |
| Still body temperature | = 225 ± 5° C. |
| Condenser temperature | = 136 ± 2° C. |
| Wiper speed setting | = 4 |
| Feed pump setting | = 2–4 |

EXAMPLE 3

Preparation of Octylphenyl N,N-diisobutylcarbamoyl Phosphine Oxide

Octylphenyl N,N-diisobutylcarbamoyl phosphine oxide was prepared by reacting octylphenyl phosphine oxide with N,N-diisobutylchloroacetamide under basic conditions using phase transfer conditions. The octyl phenyl phosphine oxide (357.5 grams) was added over a two hour period to a solution of 308.5 grams of N,N-diisobutylchloroacetamide in 600 ml. of $CH_2Cl_2$ and 300 ml. of a 50% NaOH solution containing 3.5 grams of "Adogen 464." A stirring rate of 250 rpm and a temperature of 35° C. to 40° C. was used. The reaction was continued until all the octyl phenyl phosphine oxide was consumed as determined by a GC analysis of the mixture. The reaction mixture was diluted with water. The organic layer was separated, dried over anhydrous $MgSO_4$ and stripped of solvent to give a crude product.

EXAMPLE 4

Purification of Octylphenyl N,N-diisobutylcarbamoyl Phosphine Oxide

Crude octylphenyl N,N-diisobutylcarbamoyl phosphine oxide from Example 3 was distilled using a 2' wipe film evaporator unit under the following conditions:

| | |
|---|---|
| Wall Temperature | 240–270° C. |
| Condenser Temperature | 168–172° C. |
| Vacuum | 0.1–0.3 mm Hg |

The product was obtained as a very light yellow thick liquid which crystallized on storage at room temperature after a few weeks.

EXAMPLE 5

Extraction Coefficient of CMP

The coefficient of back extraction of americium ($K_DAm$) was measured for samples of CMP purified according to this invention using a wipe film evaporator, and for samples of CMP purified by conventional small scale laboratory distillation. The concentration of CMP in this example was 0.75 M in 1.0 M tributylphosphate in a hydrocarbon solvent at 25° C.

The $K_DAm$ for twelve samples purified using the thin film evaporator ranged from 0.05 to 0.08 from 0.27 M $HN0_3$. The $K_DAm$ for samples purified by conventional small scale laboratory distillation ranged from 0.4 to 2. (Large scale commercial distillation would certainly result in even higher coefficients.) An extraction coefficient greater than 0.3 was considered to be unexceptable. Thus, the samples purified according to this invention had extraction coefficients which were 8 to 25 times better than the extraction coefficients of samples purified by conventional small scale laboratory distillation.

EXAMPLE 6

Extraction Coefficient of CMPO

The of back extraction of americium ($K_DAm$) was measured for samples of CMPO purified according to this invention using a wipe film evaporator, and for a sample of CMPO purified only by crystallization. Samples purified according to this invention had extraction coefficients that were 8 to 10 times better than the extraction coefficient of the sample purified only by crystallization.

What is claimed is:

1. A process for purifying a compound having the general formula

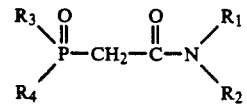

where $R_1$ and $R_2$ are each independently selected from alkyl from $C_1$ to $C_8$, and $R_3$ and $R_4$ are R or RO, where each R is independently selected from alkyl, aryl, aralkyl, and alkaryl from $C_1$ to $C_{15}$, comprising distilling said compound in a thin film evaporator having an internal heated condenser, where said distilling is performed at an evaporation temperature of about 180 to about 300° C. and a condensation temperature of about 130 to about 155° C. at a vacuum of less than 1.0 mm Hg., whereby said compound is condensed while higher-boiling impurities are not evaporated and lower-boiling impurities are not condensed.

2. A process according to claim 1 where $R_3$ and $R_4$ are both RO.

3. A process according to claim 2 wherein, prior to said distilling, said extractant is acidified with concentrated hydrochloric acid and is then treated with an aqueous solution of sodium hydroxide.

4. A process according to claim 1 wherein each $R_1$ and $R_2$ is independently selected from $C_2$ to $C_4$.

5. A process according to claim 1 wherein $R_3$ and $R_4$ are both R.

6. A process according to claim 1 wherein each R is independently selected from $C_4$ to $C_8$.

7. A process according to claim 1 wherein said thin film evaporator is a wipe film evaporator.

8. A process for purifying a dihexyl N,N-diethylcarbamoylmethylphosphonate reaction product which is formed by the reaction of dihexylphosphite and N,N-diethylchloroacetamide, said process comprising the steps of
(a) acidifying said reaction product by reaction with concentrated hydrochloric acid;
(b) treating the acidified reaction product with a 10% aqueous solution of sodium hydroxide; and
(c) distilling the reaction product from (b) in a thin film evaporator having an internal heated condenser, where said distilling is performed at an evaporation temperature of about 180 to about 300° C. and a condensation temperature of about 130 to about 155° C. at a vacuum of less than 1.0 mm Hg., whereby said compound is condensed while higher-boiling impurities are not evaporated and lower-boiling impurities are not condensed.

9. A process according to claim 8 wherein the reaction of dihexylphosphite and N,N-diethylchloroacetamide occurs in a two-phase system using a phase transfer catalyst.

10. A process according to claim 9 wherein the phase transfer catalyst is methyl tricaprylylammonium chloride.

11. A process according to claim 9 wherein the two phases are water and methylene chloride.

12. A process according to claim 8 wherein said thin film evaporator is a wipe film evaporator.

13. A process for purifying a compound having the general formula

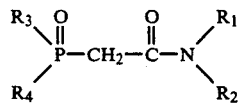

where $R_1$ and $R_2$ are independently selected from alkyl from $C_2$ to $C_4$, and $R_3$ and $R_4$ are R or RO, where each R is independently selected from alkyl, aryl, aralkyl, and alkaryl from $C_4$ to $C_8$, comprising distilling said compound in a thin film evaporator having an internal heated condenser, where said distilling is performed at an evaporation temperature of about 180 to about 300° C. and a condensation temperature of about 130 to about 155° C. at a vacuum of less than 1.0 mm Hg., whereby said compound is condensed while higher-boiling impurities are note evaporated and lower-boiling impurities are not condensed.

14. A process according to claim 13 wherein said thin film evaporator is a wipe film evaporator.

15. A process according to claim 13 wherein $R_3$ and $R_4$ are both RO.

16. A process according to claim 13 wherein $R_3$ and $R_4$ are both R.

17. A process according to claim 13 wherein, prior to said distilling, said extractant is acidified with concentrated hydrochloric acid and is then treated with an aqueous solution of sodium hydroxide.

* * * * *

UNITED STATES PATENT AND TRADEMARK OFFICE
CERTIFICATE OF CORRECTION

PATENT NO.   :   5,001,250

DATED        :   March 19, 1991

INVENTOR(S)  :   Mohan S. Saran

It is certified that error appears in the above-identified patent and that said Letters Patent is hereby corrected as shown below:

Abstract, line 4, delete "N,N-diisobutylcarbamoyl" and substitute
-- N,N-diisobutylcarbamoylmethyl --.
Column 1, line 11, delete "N,N-diisobutylcarbamoyphosphine" and substitute
-- N,N-diisobutylcarbamoylmethyl phosphine --.
Column 3, line 39, delete "N,N-diisobutylcarbamoyl" and substitute
-- N,N-diisobutylcarbamoylmethyl --.
Column 5, line 53, delete "N,N-diisobutylcarbamoyl" and substitute
-- N,N-diisobutylcarbamoylmethyl --.
Column 5, line 56, delete "N,N-diisobutylcarbamoyl" and substitute
-- N,N-diisobutylcarbamoylmethyl --.
Column 6, line 5, delete "N,N-diisobutylcarbamoyl" and substitute
-- N,N-diisobutylcarbamoylmethyl --.
Column 6, line 7, delete "N,N-diisobutylcarbamoyl" and substitute
-- N,N-diisobutylcarbamoylmethyl --.
Column 6, line 46, after "The" insert -- coefficient --.

Signed and Sealed this

Seventeenth Day of November, 1992

Attest:

DOUGLAS B. COMER

*Attesting Officer*  *Acting Commissioner of Patents and Trademarks*